United States Patent
Frye et al.

(10) Patent No.: US 8,066,998 B2
(45) Date of Patent: Nov. 29, 2011

(54) ANTIBODIES FOR NOROVIRUS

(75) Inventors: Jane Catherine Frye, Tolono, IL (US);
Hoshin Park, Champaign, IL (US);
Myung L. Kim, Champaign, IL (US)

(73) Assignee: Kim Laboratories, Inc., Champaign, IL (US)

( * ) Notice: Subject to any disclaimer, the term of this patent is extended or adjusted under 35 U.S.C. 154(b) by 119 days.

(21) Appl. No.: 12/306,818

(22) PCT Filed: Jun. 29, 2007

(86) PCT No.: PCT/US2007/072559
§ 371 (c)(1),
(2), (4) Date: Dec. 29, 2008

(87) PCT Pub. No.: WO2008/005880
PCT Pub. Date: Jan. 10, 2008

(65) Prior Publication Data
US 2010/0215649 A1    Aug. 26, 2010

Related U.S. Application Data

(60) Provisional application No. 60/818,069, filed on Jun. 30, 2006.

(51) Int. Cl.
*A61K 39/12*    (2006.01)
*C12N 5/078*    (2010.01)
(52) U.S. Cl. ...................... 424/139.1; 435/975; 435/339
(58) Field of Classification Search .................. None
See application file for complete search history.

(56) References Cited

FOREIGN PATENT DOCUMENTS
WO        02/19986 A1     3/2002
WO    2005/030806 A2     4/2005

OTHER PUBLICATIONS

Green et al. Research 1995, vol. 37, No. 3, pp. 271-283.*
Hardy et al. J. Virol. 1995, vol. 69, No. 3, pp. 1693-1698.*
Green et al. J. Gen. Virol. 1994, vol. 75, pp. 1883-1888.*
Torche et al. Vet. immunol. Immunopathol. 2006, vol. 109, No. 3-4, pp. 209-217.*
Vance P. Lochridge, et al; "Epitopes in the P2 domain of norovirus VP1 recognized by monoclonal antibodies that block cell interactions", Journal of General Virology (2005), 86, pp. 2799-2806.
Tracy Dewese Parker, et al; "Identification of Genogroup I and Genogroup II Broadly Reactive Epitopes on the Norovirus Capsid", Journal of Virology, Jun. 2005, pp. 7402-7409, vol. 79, No. 12.
Tomoko Yoda, et al; "Precise Characterization of Norovirus (Norwalk-Like Virus)-Specific Monoclonal Antibodies with Broad Reactivity", Journal of Clinical Microbiology, Jun. 2003, pp. 2367-2371, vol. 41, No. 6.
Tomoyuki Shiota, et al; "Characterization of a Broadly Reactive Monoclonal Antibody against Norovirus Genogroups I and II: Recognition of a Novel Conformational Epitope", Journal of Virology, Nov. 2007, pp. 12298-12306, vol. 81, No. 22.

* cited by examiner

*Primary Examiner* — Bao Li
(74) *Attorney, Agent, or Firm* — McDonnell Boehnen Hulbert & Berghoff LLP

(57) ABSTRACT

Norovirus antigen peptides are described having an amino acid sequence selected from the group consisting of SEQ ID NOS: 1-16, or fragments thereof. Such peptides can be used in the preparation of antiviral therapies such as vaccines, methods of preparing antibodies to the antigen peptides, methods of using the peptides or the corresponding antibodies for detection of norovirus, and compositions of the peptides, DNA and/or antibodies. A kit for the detection of norovirus is also provided.

16 Claims, No Drawings

ANTIBODIES FOR NOROVIRUS

CROSS-REFERENCE TO RELATED APPLICATIONS

This patent application claims the benefit of U.S. Provisional Patent Application No. 60/818,069, filed Jun. 30, 2006 which is incorporated by reference.

INCORPORATION-BY-REFERENCE OF MATERIAL SUBMITTED ON COMPACT DISC

Incorporated by reference in its entirety herein is a computer-readable nucleotide/amino acid sequence listing submitted concurrently herewith and identified as follows: 3,409 bytes ASCII (Text) file named "259197_ST25.TXT," created on Jun. 29, 2007.

BACKGROUND OF THE INVENTION

Norovirus is a nonbacterial pathogen implicated in epidemic gastroenteritis. Norovirus are organized into five genetically distinct genogroups based on the genomic and capsid protein sequence of noroviruses. Human norovirus (HuNV) strains fall within genogroups GI, GII, and GIV, which are further divided into genotypes, or clusters. The GI genogroup has 8 clusters (GI.1-GI.8) while the GII genogroup has 17 (GII.1-GII.17). GIV has only one cluster, GIV.1. Each cluster is antigenically distinct from the others, and strains within each cluster are also distinct.

Identification and preparation of antibodies having broad specificity against multiple strains of norovirus is desired. Additionally, effective antiviral treatments against norovirus are desired.

BRIEF SUMMARY OF THE INVENTION

The invention provides norovirus antigen peptides having an amino acid sequence selected from the group consisting of SEQ ID NOS:1-16, or fragments thereof, methods of using such peptides in the preparation of antiviral therapies, methods of using the peptides or the resulting antibodies for detection of norovirus, and compositions of the peptides and/or antibodies.

In one aspect, the invention provides an immunogen comprising an antigen peptide having an amino acid sequence selected from the group consisting of SEQ ID NOS:1-16, or a fragment thereof, wherein the fragment comprises at least 4 continuous amino acid residues.

In another aspect, the invention provides an isolated antibody to an antigen peptide having an amino acid sequence selected from the group consisting of SEQ ID NOS:1-16, or a fragment thereof, wherein the fragment comprises at least 4 continuous amino acid residues, wherein the antibody is capable of binding to a native norovirus capsid structure or virus-like particles (VLP).

In yet another aspect, the invention provides a method for making an antibody comprising immunizing a subject with one or more peptides having an amino acid sequence selected from the group consisting of SEQ ID NOS:1-16, wherein the subject expresses an antibody to the one or more peptides following the immunization.

In a further aspect, the invention provides a vaccine comprising one or more antigen peptides selected from the group consisting of SEQ ID NOS:1-16, or a fragment thereof, wherein the fragment comprises at least 4 continuous amino acid residues; and, optionally, a carrier, wherein the carrier is conjugated to at least one of the antigen peptides.

In yet another aspect, the invention provides a vaccine comprising a vector DNA, wherein the vector DNA comprises DNA encoding one or more antigen peptides selected from the group consisting of SEQ ID NOS:1-16, or a fragment thereof, wherein the fragment comprises at least 4 continuous amino acid residues; and, optionally, a pharmaceutically acceptable carrier, adjuvant, or excipient.

The invention also provides a method of detecting intact norovirus in a sample comprising providing a sample to be tested and subjecting the sample to a reporting assay comprising one or more antibodies recognizing one or more peptide sequences selected from the group consisting of SEQ ID NOS:1-16, wherein if the reporting assay indicates a positive result, norovirus is present in the sample.

Finally, the invention provides a kit for the detection of norovirus in a sample comprising a sample collection tool; a reagent for conducting a reporting assay including one or more antibodies recognizing one or more peptide sequences selected from the group consisting of SEQ ID NOS:1-16; and instructional material for executing a test for detection of norovirus and interpreting the results.

DETAILED DESCRIPTION OF THE INVENTION

The invention provides an immunogen comprising an antigen peptide having an amino acid sequence selected from the group consisting of SEQ ID NOS: 1-16, or a fragment thereof, wherein the fragment comprises at least 4 continuous amino acid residues. The immunogen can be included in a composition further comprising a pharmaceutically acceptable carrier or excipient.

The peptides of the immunogen can be made by any method known to one of ordinary skill in the art, for example, by recombinant expression or solid phase peptide synthesis.

The immunogens of the present invention can be associated with one or more genotypes and/or clusters of norovirus, as shown in Table I.

TABLE 1

| Genotype | Clusters | Host | Sequence | |
|---|---|---|---|---|
| GI | GI.1, GI.6, GI.8 | Human | TARGRLGLRR | (SEQ ID NO: 1) |
| GI | GI.2, GI.3, GI.4, GI.5, GI.7 | Human | ARGRLGVRRI | (SEQ ID NO: 2) |
| GI | GI.3 | Human | PAGGLGIRRS | (SEQ ID NO: 3) |
| GI | All | Human | LHYVDPDTGRNLGE | (SEQ ID NO: 4) |

TABLE 1-continued

| Genotype | Clusters | Host | Sequence | |
|---|---|---|---|---|
| GII | GII.1, GII.2, GII.6, GII.7, GII.8, GII.12, GII.17 | Human | GTGNGRRRVQ | (SEQ ID NO: 5) |
| GII | GIL3, GII.7, GIL8, GII.9, GII.13, GII.14 | Human | GTGNGRRRIQ | (SEQ ID NO: 6) |
| GII | GII.4 | Human | GNGTGRRRAL | (SEQ ID NO: 7) |
| GII | GII.5 | Human | GTGNGRRRFQ | (SEQ ID NO: 8) |
| GII | GII.5, GII.6, GII.10, GII.16 | Human | GNGSGRRRMQ | (SEQ ID NO: 9) |
| GII | GII.15 | Human | GNGRRGRRREL | (SEQ ID NO: 10) |
| GII | All GII | Human | VRYVNPDTGRVLFE | (SEQ ID NO: 11) |
| GIV | GIV.1 | Human | QGRRGRVRFQ | (SEQ ID NO: 12) |
| GII | GII.11 | Porcine | GNGSGRRRAR | (SEQ ID NO: 13) |
| GIII | GIII.1 | Bovine | GRRLPRIDGY | (SEQ ID NO: 14) |
| GIII | GIII.2 | Bovine | GRRLPRLDGF | (SEQ ID NO: 15) |
| GV | GV.1 | Murine | SLATGRMLKQ | (SEQ ID NO: 16) |

In another aspect, the invention provides an isolated antibody that can bind to an antigen peptide having an amino acid sequence selected from the group consisting of SEQ ID NOS: 1-16, or a fragment thereof, wherein the fragment comprises at least 4 continuous amino acid residues, wherein the antibody is capable of binding to a native norovirus capsid structure. By "binding to" is meant a ligand-substrate interaction, which can be distinguished from background or non-specific interaction. One of ordinary skill in the art can determine the specificity by any standard means such as ELISA, immunoblot or immunoprecipitation. See, e.g., Burry, J. Histochem. Cytochem. 48:163-166 (2000). The antibody can be polyclonal or monoclonal. In some embodiments, the antibody is humanized. Humanized antibodies can be prepared by any method known to one of ordinary skill in the art, such as the method described in Co, et al., PNAS 88(7):2869-73 (1991). In a preferred embodiment, the amino acid sequence is SEQ ID NO:7. The antibody can be of any desired type, such as IgG, IgA, IgY, IgD, IgM, IgE, or one or more portions thereof, such as heavy chains, light chains, Fc or F(ab) portions.

The antibody can be capable of binding to one or more genogroups or clusters of norovirus. For example, the antibody can bind to one or more of the immunogens shown in Table I. In a preferred embodiment, the antibody can bind to GI genogroup norovirus but cannot bind to GII genogroup norovirus. For example, such an antibody can bind to one or more peptides of SEQ ID NOS:1-4, but cannot bind to SEQ ID NOS:5-11. In another preferred embodiment, the antibody can bind to GII genogroup norovirus but not to GI genogroup norovirus. For example, such an antibody can bind to one or more peptides of SEQ ID NOS:5-11 but not to SEQ ID NOS:1-4. In yet another preferred embodiment, the antibody can bind to both GI genogroup norovirus and GII genogroup norovirus. In other embodiments, the antibody can bind to GI, GII, GIII, GIV, or GV genogroup norovirus, either in combination with or to the exclusion of an ability to bind to one or more of genogroups GI-GV.

The antibody can be present in a mixture of two or more distinct antibodies to antigen peptides having amino acid sequences selected from the group consisting of SEQ ID NOS:1-16, or fragments thereof, wherein the fragments comprise at least 4 continuous amino acid residues. It is possible that each of the antibodies in the mixture is capable of binding to a native norovirus capsid structure. The antibodies in the mixture can be of any desired type, such as IgG, IgA, IgY, IgD, IgM, IgE, or one or more portions thereof, such as heavy chains, light chains, Fc or F(ab) portions. Preferably, the antibody is an IgG or IgY type antibody or a portion thereof.

The inventive antibodies or mixtures thereof can be included in a composition further comprising a pharmaceutically acceptable excipient. In a preferred embodiment the composition is included in a food substance (e.g., yogurt) for oral gastrointestinal administration. Such compositions may be particularly preferred for prophylactic use upon exposure to norovirus.

The inventive antibodies can be generated from one or more amino acid sequences selected from the group consisting of SEQ ID NOS:1-16. However, any technique known to one of ordinary skill in the art can be used to prepare the antibodies of the present invention.

The invention provides a method for making an antibody comprising immunizing a subject with one or more peptides having an amino acid sequence selected from the group consisting of SEQ ID NOS:1-16, wherein the subject expresses an antibody to the one or more peptides following the immunization. The subject can be a human or a non-human animal. The non-human animal may be any suitable animal such as a cow, pig, sheep, rabbit, cat, dog, chicken, mouse, rat, or other animal capable of producing an expressed antibody product.

In some embodiments, the method further comprises the step of collecting an expressed antibody product from the subject, and wherein the expressed antibody product comprises an antibody capable of binding to a native norovirus capsid structure. The ability of the antibody to bind to a native norovirus capsid structure can be determined by any appropriate method known to one of ordinary skill in the art, such as by ELISA or another method as described above. It will be understood that in such embodiments, the subject is typically a non-human animal. In some embodiments, the expressed antibody product is collected from the blood or serum of the animal. In a preferred embodiment, the expressed antibody product is collected from the yolk of an egg, such as a chicken egg. In some embodiments, the animal generating the expressed antibody product can be used to prepare a monoclonal antibody. Monoclonal antibodies can be prepared by any method known to one of ordinary skill in the art, such as the method described in Kohler, et al., Nature 256 (5517): 495-497 (1975).

In another aspect, the invention provides a vaccine comprising one or more antigen peptides selected from the group consisting of SEQ ID NOS:1-16, or a fragment thereof, wherein the fragment comprises at least 4 continuous amino acid residues; and, optionally, a carrier, wherein the carrier is conjugated to at least one of the antigen peptides. In a preferred embodiment, multiple copies of at least one of the peptides are conjugated to each carrier. The carrier can be any pharmaceutically acceptable carrier. In some embodiments, the carrier is a protein carrier. In other embodiments, the carrier is a lipid carrier. In a preferred embodiment, the carrier comprises a norovirus protein. For example, the carrier can be one or more copies of a norovirus capsid protein or a subunit or domain thereof, including virus-like particles (VLPs) (Jiang X, et al., J. Virol. 66(11):6527-32 (1992)), as well as a norovirus RNA polymerase protein or a subunit or domain thereof (see, e.g., Venkataram Prasad, et al., Science 286:287-290 (1999). In still other embodiments, the carrier can be any suitable carrier, such as virosomes, the hepatitis B virus core protein (HbcAg) (see, e.g., J. Virol. 79:13641 (2005)), poly (lactide-co-glycolide) microparticles, liposomes, multiple antigenic peptides (MAPs), immune-stimulating complexes (ISCOMS), chitosan, keyhole limpet hemocyanin (KLH), or bovine serum albumin (BSA).

The vaccine can further comprise one or more pharmaceutically acceptable excipients useful or necessary for formulating the vaccine for administration to a subject in, for example, a composition described herein.

In yet another aspect, the invention provides a vaccine comprising a vector DNA, wherein the vector DNA comprises DNA encoding one or more antigen peptides selected from the group consisting of SEQ ID NOS:1-16, or a fragment thereof, wherein the fragment comprises at least 4 continuous amino acid residues; and, optionally, a pharmaceutically acceptable carrier, adjuvant, or excipient.

Compositions of the present invention comprise an immunogen, antibody, or DNA of the present invention and a pharmaceutically acceptable excipient. The compositions can be, for example, a vaccine or a prophylactic, or a reagent for a diagnostic tool. The composition can be formulated for administration by any route such as intravenous, intramuscular, intraperitoneal, intranasal, percutaneous, subcutaneous, or oral. In a preferred embodiment, the composition is formulated for oral administration. The composition also can comprise additional components such as diluents, adjuvants, excipients, preservatives, and pH adjusting agents, and the like.

The compositions of the present invention can be formulated for oral administration, including as a food or beverage (e.g., yogurt). Alternatively, the compositions can be formulated as a tablet, capsule, pill, syrup, elixir, or other vehicle for oral administration.

Formulations suitable for local or systemic injectable administration include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, or tablets.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described, for example, in Martin et al., J. Biol. Chem., 257: 286-288 (1982) via a disulfide interchange reaction.

Administration into the airways can provide either systemic or local administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

In some embodiments, administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, suppositories, mouthwashes, rapidly dissolving tablets, or lozenges.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide] and the like. Particular formulations using drug delivery systems can be in the form of liquid suspensions, ointments, complexes to a bandage, collagen shield or the like.

In another aspect, the invention provides a method of detecting intact norovirus in a sample comprising: (a) providing a sample to be tested; and (b) subjecting the sample to a reporting assay employing one or more antibodies recognizing one or more peptide sequences selected from the group consisting of SEQ ID NOS:1-16, wherein if the reporting assay indicates a positive result, norovirus is present in the sample. The sample can be taken from any source where detection of norovirus is useful or necessary. For example, the sample can be a water sample, a food sample, an environmental sample, or a specimen sample. The specimen can be an animal tissue sample or a sample of an animal bodily fluid or waste product.

In some embodiments, the norovirus which is sought to be detected is of a genotype generally found in human hosts. In other embodiments, the norovirus is of a genotype generally found in bovine hosts. The norovirus can also be of a genotype generally found in murine or porcine hosts.

In yet another aspect, the invention provides a kit for the detection of intact norovirus in a sample comprising: (a) a sample collection tool; (b) reagents for conducting a reporting assay comprising one or more antibodies recognizing one or more peptide sequences selected from the group consisting of SEQ ID NOS:1-16; and (c) instructional material for executing a test for detection of norovirus and interpreting the results.

The reporting assay used in the methods or kits of the present invention can be any reporting assay known in the art or later developed. The assay can be, for example, any type of ELISA, or an assay such as described in U.S. Publication No. 2006-0129327. The assay can also be immunomagnetic separation (IMS) (Myrmel, et al., Int. J. Food. Microbiol. 62(1-2):17-26 (2000). Detection of the antibodies using IMS can be performed, for example, using a ValidCheck apparatus (as described in PCT/US07/66172).

The following examples further illustrate the invention but, of course, should not be construed as in any way limiting its scope.

Example 1

This example demonstrates the preparation and use of antigenic norovirus peptide sequences.

Preparation: Antigenic norovirus peptide sequences are synthesized at the Protein Sciences Facility at the University of Illinois at Urbana-Champaign Biotechnology Center. The peptides are named KLp1, KLp2, KLp3, etc. The amino acid cysteine is added to the N-terminus of each peptide in order to facilitate binding to carrier proteins, a chemical reaction which results in a covalent bond generated between the sulfhydryl functional groups located in the side chains of the cysteines and activated amine groups located on lysine side chains on carrier proteins. KLH (Keyhole Limpet Hemocyanin)-peptide and BSA (Bovine Serum Albumin)-peptide conjugated antigens are generated, characterized, and purified according to the protocols described in the Inject Maleimide Activated Immunogen Conjugation Kit with mcKLH and BSA from Pierce (Rockford, Ill.). The KLH-peptide conjugates are used as immunogens in mice, while the BSA-peptide conjugates are used to test for the presence of anti-peptide antibodies in the resulting polyclonal sera. The KLH immunogen conjugates are named KLH-1, KLH-2, KLH-3, etc. The BSA test conjugates are named BSA-1, BSA-2, BSA-3, etc. Virus-like particles (VLPs) for norovirus are obtained from NIH and CDC.

Administration in animals: For the primary immunizations, individual Balb/c mice are injected intraperitoneally with emulsions comprising 30 μg of one of the KLH-peptide conjugates, 10 μg of the Balb/c T-cell epitope NTGGAWDNAKKY (SEQ ID NO:17), a portion of a microbial pyrophosphatase protein sequence (such as Accession No. Q9ZWI8), and TiterMax Gold Adjuvant (Sigma, St. Louis, Mo.). For all subsequent immunizations, the same procedure is followed except the adjuvant is Incomplete Freund's (Sigma, St. Louis, Mo.). The total volume amount injected into each mouse does not exceed 100 μl, with the adjuvant being 50% of the volume. Immunizations are 3 weeks apart. After mice are immunized 2-3 times, blood samples are taken via the retro-orbital plexus while the mice are under the influence of a general anesthesia. Using an enzyme-linked immunosorbent assay (ELISA), the polyclonal sera are tested for reactivity to the BSA-peptide test conjugates. Sera with strong responses to these antigens are further tested for reactive isotype on VLP using ELISA.

Sera obtained from mice injected with the KLH-peptide conjugates are found to be reactive to the BSA-peptide conjugates as well as norovirus VLP.

Example 2

This example demonstrates the preparation of monoclonal antibodies to norovirus immunogens.

Mice are immunized with KLH-peptide immunogens as described in Example 1. Immunized mice showing a high titer IgG serum antibody response on VLP antigens are sacrificed for hybridoma fusion. The cell fusion process follows standard protocols similar to those first described by Kohler and Milstein in 1975 (Kohler, et al., Nature 256 (5517): 495-497, 1975), in which lymphocytes isolated from the spleen are fused with sp2/0 myeloma cells in the presence of polyethylene glycol. Resulting hybridoma cell lines are grown in selective HAT (Hypoxanthine Aminopterin-Thymidine) media (Dulbecco's Modified Eagle's Medium (DMEM) with L-glutamine supplemented with 10% FBS (Fetal Bovine Serum), NCTC, Minimum Essential Media (MEM) nonessential amino acids, cysteine, hypoxanthine, aminopterin, thymidine, oxaloacetic acid, sodium pyruvate, insulin, and kanamycin) in a 7.2% $CO_2$ incubator. Seven to fourteen days after fusion, culture media from the hybridoma cell lines are screened for the presence of IgG monoclonal antibodies able to bind norovirus VLP reagents on ELISA. Hybridoma cell lines displaying the desired traits are subcloned for stability, and then grown in Integra Celline bioreactors for large-scale monoclonal antibody production. The resulting bioreactor antibody is purified on protein G columns and stored in PBS (Phosphate Buffer Saline) with 0.02% sodium azide at 4° C.

Example 3

This example demonstrates the use of antibodies in detecting norovirus using a simple ELISA.

An Immulon I B plate (Thermo Fisher, PA) is coated with norovirus or VLPs in PBS at 2 µg/ml. The plate is incubated at 37° C. for 1 hour and washed. The wells are then blocked with 0.5% skim milk in PBS and incubated at 37° C. for at least 1 hour. Then 50 µl (5 µg/ml) of the corresponding anti-norovirus monoclonal antibody (prepared as described in Example 2) is conjugated to HRP (Horse Radish Peroxidase) using the Surelink conjugation kit (KPL, MD) and added to each well, incubated at 37° C. for 1 hour and washed. 100 µl of TMB (Tetramethylbenzidine) substrate (Sigma, MA) is added to all the wells and after a blue color change is observed $H_2SO_4$ is added to stop the reaction. The plate is read at 450 nm absorbance.

Results: Monoclonal antibodies (mAbs) generated against the peptide of SEQ ID NO:1 detect the GI.1 VLP (Norwalk) on ELISA. It is predicted that a similar detecting ability will be seen on VLPs (or native norovirus) representing genotypes GI.6 and GI.8. MAbs generated against peptide of SEQ ID NO:2 are able to detect the GI.3 VLP Desert Shield) on ELISA. Similar detecting ability will be seen on VLPs or native norovirus representing the remaining GI genotypes GI.2, GI.4, GI.5, and GI.7. MAbs generated against the peptide of SEQ ID NO:6 detect various GII VLPs on ELISA including GII.2, GII.3, and GII.7. Anti-peptides of SEQ ID NO:7 mAbs respond strongly to GII..4, but not the other GII VLPs. Table 2 shows the reactivity pattern of initial anti-peptide monoclonal antibodies on selected norovirus VLPs (ELISA).

Example 4

This example demonstrates the use of antibodies in capturing and detecting norovirus by Sandwich ELISA.

The wells of Immulon 2HB plates (Thermo Fisher, PA) are coated with 50 µl of an anti-norovirus antibody (at 250 ng/well), prepared as in Example 2, incubated at 37° C. for 1 hour and washed. The wells are then blocked with 0.5% milk in PBS and incubated at 37° C. for at least 1 hour. The prepared samples are added to the wells. The plate is incubated at 37° C. for 1 hour and washed. The anti-norovirus antibody is conjugated to HRP using the Surelink conjugation kit (KPL, MD) and 50 µl of anti-norovirus-HRP (at 5 µg/ml) is added to each well. The plate is then incubated at 37° C. for 1 hour and washed. 100 µl of TMB substrate is added to all the wells and after a blue color change is observed $H_2SO_4$ is added to stop the reaction. The plate is read at 450 nm.

Positive intensity results relative to background are obtained upon analysis of the plate.

Example 5

This example demonstrates the use of antibodies in concentrating and detecting norovirus by IMS-ELISA.

The IMS-ELISA procedure is performed by blocking the eppendorf tubes with 0.5% milk in PBS and incubated at 37° C. for 1 hour. Norovirus VLPs are added to each tube along with the antibody/bead conjugate. The antibody/bead conjugate is the anti-norovirus antibody, prepared as in Example 2, that is conjugated to M280 tosylactivated dynal beads from Invitrogen using the protocol that is recommended from Invitrogen. The tubes are then incubated at room temperature for 1 hour with rotation. A magnetic retriever is used to pull the IMS complex (VLPs bound on Magnetic beads) to one side. The beads are washed once with PBS and resuspended in 100 µl PBS. The IMS complex of each tube is then transferred to Immulon I B plate coated with anti-norovirus antibody. The plate is incubated at 37° C. for 1 hour and washed. Then 50 µl (2 µg/ml) of the anti-norovirus antibody conjugated to HRP (Horse Radish Peroxidase) using the Surelink conjugation kit (KPL, MD) are added to each well, incubated at 37° C. for 1 hour and washed. 100 µl of TMB (Tetramethylbenzidine) substrate (Sigma, MA) is added to all the wells. After a blue color change is observed, $H_2SO_4$ is added to stop the reaction. The plate is read at 450 nm absorbance.

Positive intensity results relative to background are obtained upon analysis of the plate.

Example 6

This example demonstrates the use of antibodies in concentrating and detecting norovirus by immunomagnetic separation.

TABLE 2

| Immunized peptide sequence | mAb name | GI.1 Norwalk | GI.3 Desert Shield | GII.1 Hawaii | GII.2 Snow Mountain | GII.3 Toronto | GII.4 MD145 | GII.5 White River | GII.6 Florida | GII.7 Gwynedd |
|---|---|---|---|---|---|---|---|---|---|---|
| SEQ ID NO: 1 | P2B2 | +++ | − | − | − | − | − | − | − | − |
| SEQ ID NO: 1 | P3H6 | +++ | − | − | − | − | − | − | − | − |
| SEQ ID NO: 2 | P1A6 | − | +++ | − | − | − | − | − | − | − |
| SEQ ID NO: 2 | P1A7 | − | +++ | − | − | − | − | − | − | − |
| SEQ ID NO: 2 | P1A8 | − | +++ | − | − | − | − | − | − | − |
| SEQ ID NO: 2 | P1A9 | − | +++ | − | − | − | − | − | − | − |
| SEQ ID NO: 4 | P9B3 | − | − | − | +++ | +++ | − | − | − | +++ |
| SEQ ID NO: 5 | P3B11 | − | − | − | − | − | +++ | − | − | − |
| SEQ ID NO: 5 | P4B8 | − | − | − | − | − | +++ | − | − | − |

The IMS procedure is performed by blocking microcentrifuge tubes with 0.5% milk in PBS and incubated at 37 C for 1 hour. Norovirus VLPs are added to each tube along with the antibody/bead conjugate. The antibody/bead conjugate is the anti-norovirus antibody, prepared as in Example 2, that is conjugated to M280 tosylactivated dynal beads from Invitrogen using the protocol that is recommended from Invitrogen. The tubes are then incubated at room temperature for 1 hour with rotation. After one hour of incubation a magnetic retriever is used to pull the IMS complex (VLPs bound on Magnetic beads) to one side. The beads are washed 1 time with PBS and resuspended with 300 µl (2.5 µg/ml) of the anti-norovirus antibody conjugated to HRP (Horse Radish Peroxidase) using the Surelink conjugation kit (KPL, MD). The tubes are incubated at 37° C. for 1 hour with rotation and washed 3 times with PBS using the magnetic retriever. 100 µl of TMB (Tetramethylbenzidine) substrate (Sigma, MA) is added to all the wells. After a blue color change is observed, $H_2SO_4$ is added to stop the reaction. The plate is read at 450 nm absorbance.

Positive intensity results relative to background are obtained upon analysis of the plate.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An isolated antibody that binds to an antigen peptide consisting of an amino acid sequence selected from group consisting of SEQ ID NOS: 5-9, wherein the antibody binds to a norovirus capsid.

2. The antibody of claim 1, wherein the antibody is polyclonal or monoclonal.

3. The antibody of claim 1, wherein the antibody is humanized.

4. The antibody of claim 1, wherein the antibody is capable of binding to GII genogroup norovirus but not capable of binding to GI genogroup norovirus.

5. The antibody of claim 1, wherein the antibody is generated from one or more amino acid sequences selected from the group consisting of SEQ ID NOS: 5-9.

6. The antibody of claim 1, wherein the antibody is present in a mixture of two or more distinct antibodies to antigen peptides consisting of amino acid sequences selected from the group consisting of SEQ ID NOS: 5-9, wherein a plurality of antibodies in the mixture are capable of binding to a norovirus capsid.

7. A composition comprising the antibody of any of claims 1-2, 3, 4, and 5-6, further comprising a pharmaceutically acceptable excipient.

8. The composition of claim 7, wherein the composition is formulated for oral administration.

9. The composition of claim 7, wherein the antibody type is eqg yolk immunoglobulin (IgY).

10. A kit for the detection of intact norovirus in a sample comprising: (i) a sample collection tool; and (ii) reagents for conducting a reporting assay including one or more antibodies recognizing one or more antigen peptides consisting of an amino acid sequence set forth in SEQ ID NOS: 5-9.

11. A method for making an antibody comprising immunizing a subject with one or more peptides consisting of an amino acid sequence selected from the group consisting of SEQ ID NOS:5-9, wherein the subject expresses an antibody to the one or more peptides following the immunization.

12. The method of claim 11, further comprising the step of collecting an expressed antibody product from the subject, wherein the subject is a non-human animal, and wherein the expressed antibody product comprises an antibody capable of binding to a norovirus capsid.

13. The method of claim 12, further comprising the step of preparing a monoclonal antibody from the expressed antibody product.

14. A method of detecting intact norovirus in a sample comprising: (i) providing a sample to be tested; and (ii) subjecting the sample to a reporting assay employing one or more antibodies that bind to one or more antigen peptides consisting of an amino acid sequence set forth in SEQ ID NOS: 5-9, wherein if the reporting assay indicates a positive result, then norovirus is present in the sample.

15. The method of claim 14, wherein the sample is selected from the group consisting of a water sample, a food sample, an environmental sample, and a specimen sample.

16. The method of claim 14, wherein the norovirus is a human norovirus.

* * * * *

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Thr Ala Arg Gly Arg Leu Gly Leu Arg Arg
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic

<400> SEQUENCE: 2

Ala Arg Gly Arg Leu Gly Val Arg Arg Ile
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic

<400> SEQUENCE: 3

Pro Ala Gly Gly Leu Gly Ile Arg Arg Ser
1               5                   10
```

```
<210> SEQ ID NO 4
<211> LENGTH: 14
<212> TYPE: PRT
<213> ORGANISM: Artificial
<220> FEATURE:
<223> OTHER INFORMATION: Synthetic

<400> SEQUENCE: 4

Leu His Tyr Val Asp Pro Asp Thr Gly Arg Asn Leu Gly Glu
1               5                   10

<210> SEQ ID NO 5
<211> LENGTH: 10
<212> TYPE: PRT
<213> ORGANISM: Artificial
<220> FEATURE:
<223> OTHER INFORMATION: Sysnthetic

<400> SEQUENCE: 5

Gly Thr Gly Asn Gly Arg Arg Arg Val Gln
1               5                   10

<210> SEQ ID NO 6
<211> LENGTH: 10
<212> TYPE: PRT
<213> ORGANISM: Artificial
<220> FEATURE:
<223> OTHER INFORMATION: Synthetic

<400> SEQUENCE: 6

Gly Thr Gly Asn Gly Arg Arg Arg Ile Gln
1               5                   10

<210> SEQ ID NO 7
<211> LENGTH: 10
<212> TYPE: PRT
<213> ORGANISM: Artificial
<220> FEATURE:
<223> OTHER INFORMATION: Synthetic

<400> SEQUENCE: 7

Gly Asn Gly Thr Gly Arg Arg Arg Ala Leu
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic

<400> SEQUENCE: 8

Gly Thr Gly Asn Gly Arg Arg Arg Phe Gln
1               5                   10

<210> SEQ ID NO 9
<211> LENGTH: 10
<212> TYPE: PRT
<213> ORGANISM: Artificial
<220> FEATURE:
<223> OTHER INFORMATION: Synthetic

<400> SEQUENCE: 9

Gly Asn Gly Ser Gly Arg Arg Arg Met Gln
1               5                   10
```

```
<210> SEQ ID NO 10
<211> LENGTH: 11
<212> TYPE: PRT
<213> ORGANISM: Artificial
<220> FEATURE:
<223> OTHER INFORMATION: Synthetic

<400> SEQUENCE: 10

Gly Asn Gly Arg Arg Gly Arg Arg Arg Glu Leu
1               5                   10

<210> SEQ ID NO 11
<211> LENGTH: 14
<212> TYPE: PRT
<213> ORGANISM: Artificial
<220> FEATURE:
<223> OTHER INFORMATION: Synthetic

<400> SEQUENCE: 11

Val Arg Tyr Val Asn Pro Asp Thr Gly Arg Val Leu Phe Glu
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Gln Gly Arg Arg Gly Arg Val Arg Phe Gln
1               5                   10

<210> SEQ ID NO 13
<211> LENGTH: 10
<212> TYPE: PRT
<213> ORGANISM: Artificial
<220> FEATURE:
<223> OTHER INFORMATION: Synthetic

<400> SEQUENCE: 13

Gly Asn Gly Ser Gly Arg Arg Arg Ala Arg
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic

<400> SEQUENCE: 14

Gly Arg Arg Leu Pro Arg Ile Asp Gly Tyr
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Gly Arg Arg Leu Pro Arg Leu Asp Gly Phe
1               5                   10
```

```
<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Ser Leu Ala Thr Gly Arg Met Leu Lys Gln
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic

<400> SEQUENCE: 17

Asn Thr Gly Gly Ala Trp Asp Asn Ala Lys Lys Tyr
1               5                   10
```